United States Patent [19]

Williamson et al.

[11] Patent Number: 5,358,969
[45] Date of Patent: Oct. 25, 1994

[54] METHOD OF INHIBITING NITRIC OXIDE FORMATION

[75] Inventors: Joseph R. Williamson, Town and Country; John A. Corbett, St. Louis; Michael L. McDaniel, Glendale; Ronald G. Tilton, St. Louis, all of Mo.

[73] Assignee: Washington University, St. Louis, Mo.

[21] Appl. No.: 110,915

[22] Filed: Aug. 24, 1993

Related U.S. Application Data

[63] Continuation-in-part of Ser. No. 843,387, Feb. 28, 1992, Pat. No. 5,246,971, and a continuation-in-part of Ser. No. 906,632, Jun. 30, 1992, Pat. No. 5,246,970, each is a continuation-in-part of Ser. No. 807,912, Dec. 16, 1991, abandoned.

[51] Int. Cl.⁵ .............................. A61K 31/155
[52] U.S. Cl. .................... 514/632; 514/634
[58] Field of Search .................... 514/634, 632

[56] References Cited

U.S. PATENT DOCUMENTS

| | | | |
|---|---|---|---|
| 4,544,670 | 10/1985 | Studt et al. | 514/617 |
| 4,758,583 | 7/1988 | Cerami et al. | 514/399 |
| 4,870,210 | 9/1989 | Musser | 564/228 |
| 4,983,604 | 1/1991 | Ulrich et al. | 514/238.5 |
| 5,128,360 | 7/1992 | Cerami et al. | 514/400 |
| 5,246,970 | 9/1993 | Williamson et al. | 514/632 |

FOREIGN PATENT DOCUMENTS 450598 10/1991 European Pat. Off. .

OTHER PUBLICATIONS

Bredt et al., Nature 351, 714–718 (1991).
Moncada et al., Pharmacol. Rev. 43, 109–142 (1991).
Brownlee et al., Science 232, 1629–1632 (1986).
Bucala et al., J. Clin. Invest. 87, 432–438 (1991).
Tilton et al., Invest. Ophthalmol. Vis. Sci. 31, 342 (1990).
Williamson et al., Diabetes & Metabolisme 16, 369–370 (1990).
Chang et al., Diabetes 40 (Supp. 1) 210A (1991).
Corbett et al., J. Biol. Chem. 266, 21351–21354 (1991).
Chem. Absts. 115: 248104, of Griffith WO 91 04,023 (1989).

*Primary Examiner*—Raymond J. Henley, III
*Attorney, Agent, or Firm*—Scott J. Meyer

[57] ABSTRACT

A method is disclosed for inhibiting nitric oxide formation in a warm blooded mammal afflicted with an acute or chronic inflammatory disease which comprises administering to said mammal an effective nitric oxide inhibitory amount of methyl-, or 1,1-dimethyl-, or amino-substituted guanidines.

10 Claims, 4 Drawing Sheets

METHOD OF INHIBITING NITRIC OXIDE FORMATION

ACKNOWLEDGEMENT OF GOVERNMENT SUPPORT

This work was supported in part by National Institutes of Health grants DK06181, T32 DK07296, EY006600, HL39934, and DK20579.

CROSS-REFERENCE TO RELATED APPLICATIONS

This is a continuation-in-part of application Ser. No. 07/843,387, filed Feb. 28, 1992 and now U.S. Pat. No. 5,246,971, a continuation-in-part application Ser. No. 07/906,632, filed Jun. 30, 1992, now U.S. Patent 5,246,970 each of which are a continuation-in-part of application Ser. No. 07/807,912, filed Dec. 16, 1991 now abandoned.

BACKGROUND OF THE INVENTION

This invention relates to a method of inhibiting nitric oxide formation in warm blooded mammals and, more particularly, to the administration of methyl-, dimethyl-, or amino-substituted guanidines as inhibitors of nitric oxide production in a host afflicted with acute or chronic inflammatory disease.

Nitric oxide synthase catalyzes the mixed functional oxidation of L-arginine to L-citrulline and nitric oxide (NO·) [Stuehr et al., Proc. Natl. Acad. Sci. USA 88, 7773 (1991)]. NO· appears to function as either a signaling or an effector molecule depending on the isoform of the enzyme. The constitutive isoform of nitric oxide synthase produces small amounts of NO· which activate guanylate cyclase resulting in the formation of cGMP which mediates endothelium-dependent relaxation [Moncada et al., Pharmacol. Reviews 43, 109 (1991)] and neural transmission [Garthwaite, Trends Neurol. Sci. 14, 60 (1991)]. NO· is produced in much larger amounts by the cytokine and endotoxin inducible isoform of nitric oxide synthase, and in macrophages functions as an effector molecule which appears to mediate the cytotoxic actions of macrophages on target cells [Hibbs et al., Nitric Oxide from L-Arginine: a Bioregulatory System, S. Moncada and E. Higgs, Eds. Elsevier, N.Y. pp. 189–223 (1990)]. Since NO· is a potent vasodilator and increases blood flow, and since vasoactive agents (such as histamine and bradykinin), which stimulate NO· production increase both blood flow and vascular permeability, NO· may be a candidate for mediating increases in blood flow and vascular permeability induced by diabetes and elevated glucose [Pugliese et al., Diabetes/Metabolism Reviews 7, 35 (1991)].

Recently, Interleukin-1 (IL-1) has been shown to induce the expression of the cytokine inducible isoform of nitric oxide synthase in pancreatic islets. The production of NO· has been proposed to be the effector molecule which mediates IL-1's inhibitory effects on islet function [Southern et al., FEBS. Lett. 276, 42 (1990) and Corbett et al., Biochemical J. 287, 229 (1992)]. Generation of an IL-1-induced EPR detectable iron-nitrosyl complex, which is prevented by $N^G$-monomethyl-L-arginine (NMMA), has been used to confirm the formation of nitric oxide by islets [Corbett et al., J. Biol. Chem. 266, pp. 21351–21354 (1991)]. Also, the protein synthesis inhibitor, cycloheximide has been shown to block IL-1-induced nitrite formation, cGMP accumulation, and EPR detectable iron-nitrosyl complex formation by islets, thus establishing that IL-1 induces the cytokine inducible isoform of nitric oxide synthase in pancreatic islets [Corbett et al., Biochemical J. 287, 229 (1992)].

The pathogenesis of diabetic complications has been linked to imbalances in sorbitol, myo-inositol, and 1,2-diacyl-sn-glycerol metabolism, and to non-enzymatic glycation of cellular and extracellular constituents [Pugliese et al., Diabetes/Metabolism Reviews 7, 37 (1991)]. The glycation link is supported by evidence that aminoguanidine, a nucleophilic hydrazine compound, interferes with the formation of these glycation products and also attenuates the development of several diabetes-induced vascular [Pugliese et al., Diabetes/-Metabolism Reviews 7, 35 (1991); Williamson et al., Diabete & Metab. 16, 3369 (1990); Soulis-Liparota et al., Diabetes 40, 1328 (1991)], neural [Kihara et al., Proc. Natl. Acad. Sci. USA 88, 6107 (1991)] and collagen changes [Brownlee et al., New Engl. J. Med. 318, 1315 (1988) and Brownlee et al., Science 232, 1629 (1986)]. Bucala et al., J. Clin. Invest. 87, 432 (1991) recently, reported that quenching of NO· in vitro by glycated albumin is attenuated by aminoguanidine (present during exposure of albumin to glycating agents) and suggested that glycation products may impair endothelium-dependent relaxation by attenuating NO· activity.

BRIEF DESCRIPTION OF THE INVENTION

Figure 1:
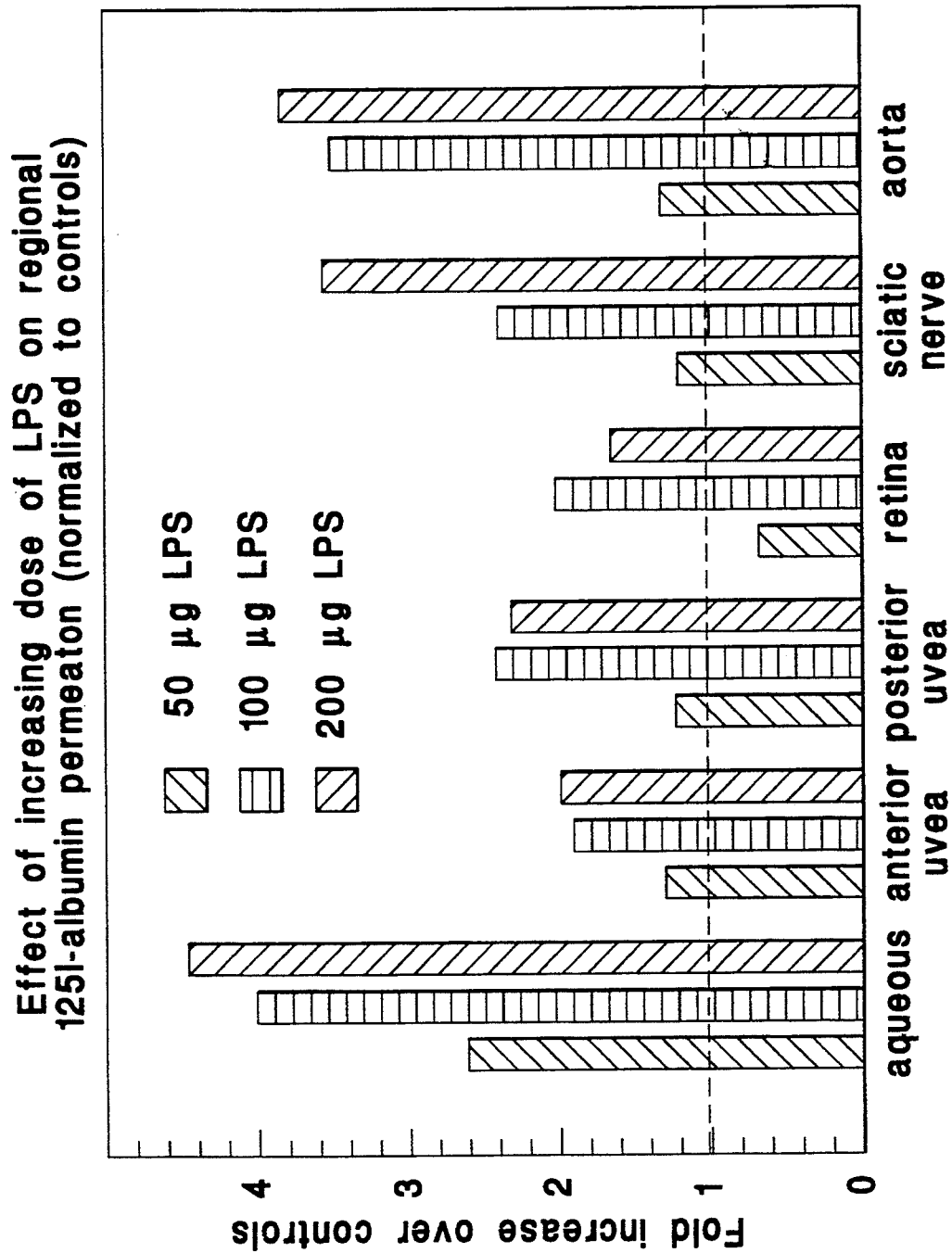
FIG. 1 is a bar graph showing the effects of increasing the dose of lipopolysaccharide (LPS) on regional $^{251}$I-albumin permeation.

In accordance with the present invention a novel method of inhibiting nitric oxide formation in warm blooded mammals afflicted with acute or chronic inflammatory diseases is provided. The method comprises administering to warm blooded mammals afflicted with acute or chronic inflammatory diseases a small but nitric oxide inhibitory effective amount of methyl-, dimethyl-, or amino-substituted guanidines. These inhibitory compounds are also chemically named as aminoguanidine, N,N'-diaminoguanidine, methylguanidine and 1,1-dimethylguanidine.

It will be understood that pharmaceutically acceptable salts of these compounds, e.g., the HCl, $HCO_3$ and sulfate salts, can also be administered to the host in accordance with the method of the invention.

Inflammation can be conveniently divided into acute and chronic conditions. Acute inflammation is generally of relatively short duration and lasts for about a few minutes to about one to two days. Its main characteristics are increased blood flow, exudation of fluid and plasma proteins (edema) and emigration of leukocytes, predominantly neutrophils. Chronic inflammation is of longer duration and is associated histologically with the presence of lymphocytes and macrophages and with proliferation of blood vessels and connective tissue.

Inflammation is manifested by heat, redness, swelling, pain and loss of function. See, e.g. Cotran, Kumar and Robbins, *Robbins Pathologic Basis of Diseases*, 4th ed., W. B. Saunders Company, pp. 40–41 (1989); Chandrasoma and Taylor, *Concise Pathology*, First Edition, p. 35–44, Appleton & Lange (1991).

The causes of inflammation are numerous and include such factors as microbial infections (e.g., bacterial and fungal infections), physical agents such as burns, radiation and trauma, chemical agents such as toxin and caustic substances, necrotic tissue and various types of immunologic reactions.

The present invention is directed to the prevention/treatment of a broad spectrum of diseases which may be linked to the production of nitric oxide by leukocytes (neutrophils and macrophages) and other cells of non-hemopoietic origin as distinguished from diseases mediated by immunologic reactions as claimed in copending application Ser. No. 07/906,632. The treatment of acute inflammatory disease is particularly illustrated herein in greater detail against endotoxin-induced acute uveitis and generalized vascular leakage. In these illustrative treatments, a standard state-of-the-art animal model is used, namely the endotoxin-induced uveitis in the rat such as described by Cousins et al. *Exp. Eye Res.* 39, 665–676 (1984); Herbort et al., *Graefe's Arch. Clin. Exp. Opthalmol.* 226, 553–558 (1988). However, it will be understood that the method of the invention is not limited to the treatment of uveitis but includes treatment of other acute and chronic inflammatory diseases as mentioned above. These diseases include but are not limited to diseases such as, for example, acute and chronic infections (bacterial and fungal, including diptheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjuctivitis; acute and chronic serositis (pericarditis, peritonitis, synovitis, pleuritis and tendonitis); uremic pericarditis; acute and chronic cholecystis; acute and chronic vaginitis; drug reactions; insect bites; burns (thermal, chemical, and electrical); and sunburn.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which briefly:

FIG. 1 is a bar graph which shows the effect of increasing dose of lipopolysaccharide (LPS; endotoxin purified from *Salmonella minnesota*) on regional $^{125}$I-albumin permeation (normalized to controls). The fold increase (from 0 to in excess of 4-fold increase) over controls is shown on the y axis for various tissues indicated on the x axis at three levels of LPS., namely 50 μg, 100 μg and 200 μg LPS as a divided dose injected into both hind footpads of Lewis rats.

Figure 2:
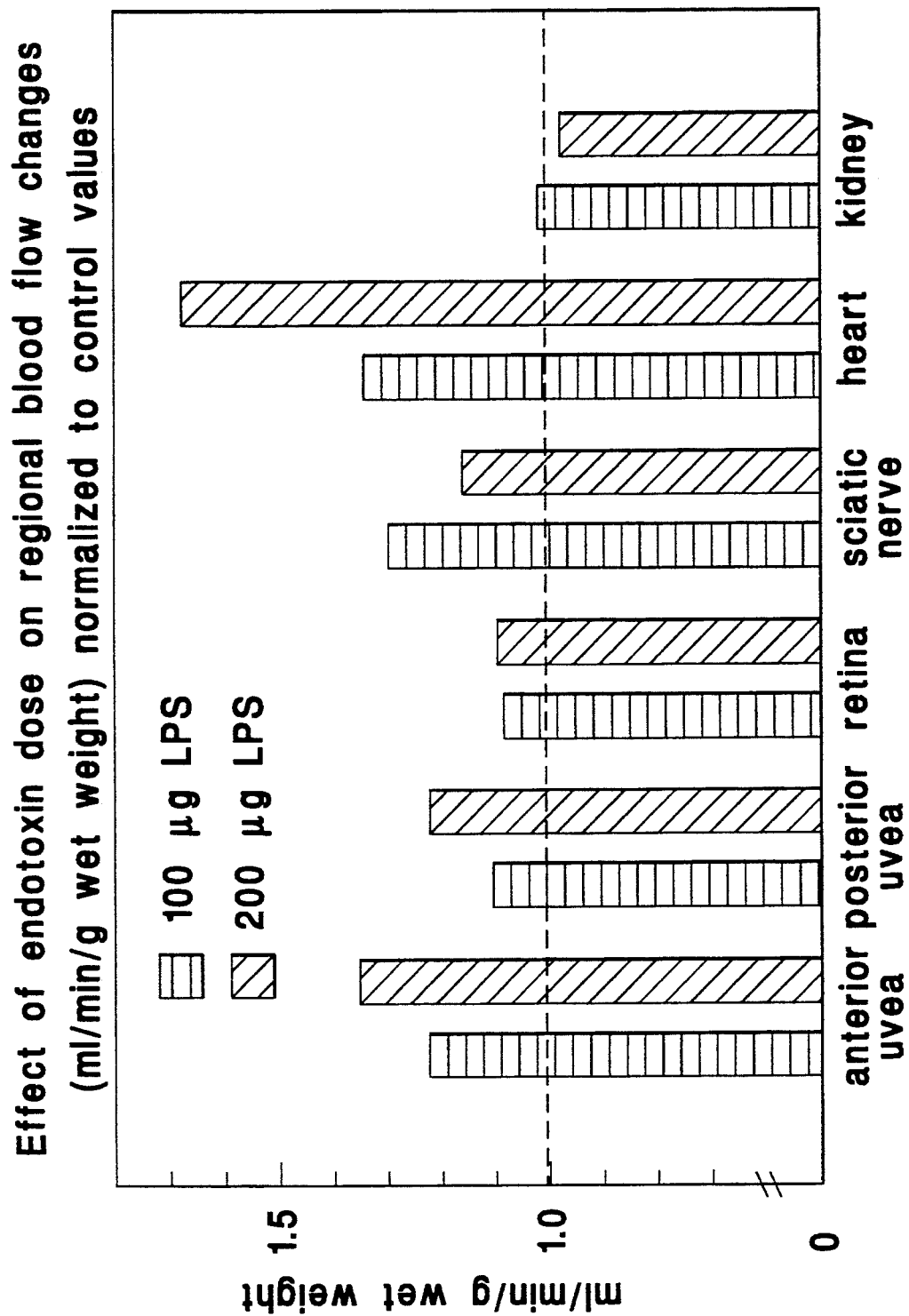
FIG. 2 is a bar graph which shows the effect of endotoxin dose on regional blood flow changes.

FIG. 2 is a bar graph which shows the effect of endotoxin dose on regional blood flow changes. Blood flow changes in ml/min/g wet weight are shown as a fold increase (from 0 to in excess of 1.5-fold increase) on the y axis for various tissues indicated on the x axis at two levels of LPS, namely 100 μg and 200 μg LPS as a divided dose injected in Lewis rats as in FIG. 1.

Figure 3A:
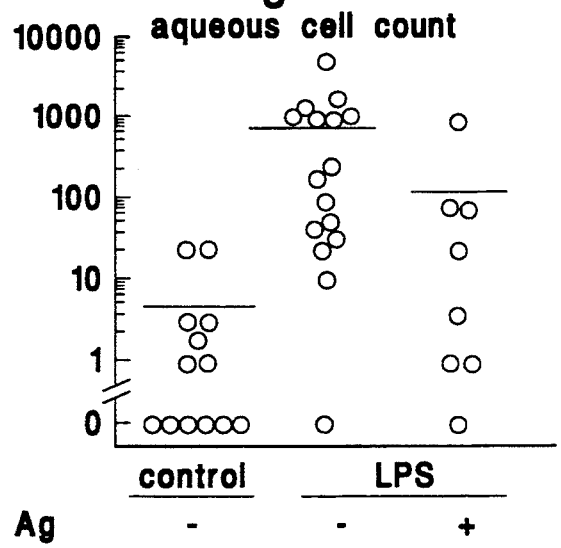
FIG. 3 in parts 3A, 3B, 3C and 3D is graphical representation which shows aqueous fluid leukocyte cell counts in Lewis rats treated with 100 µg LPS.
Figure 3B:
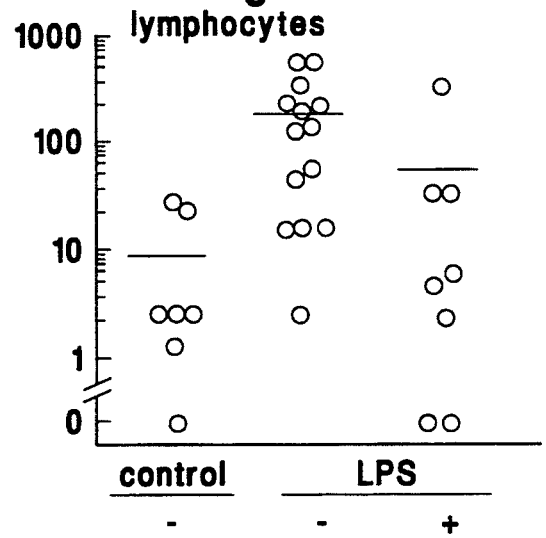
Figure 3C:
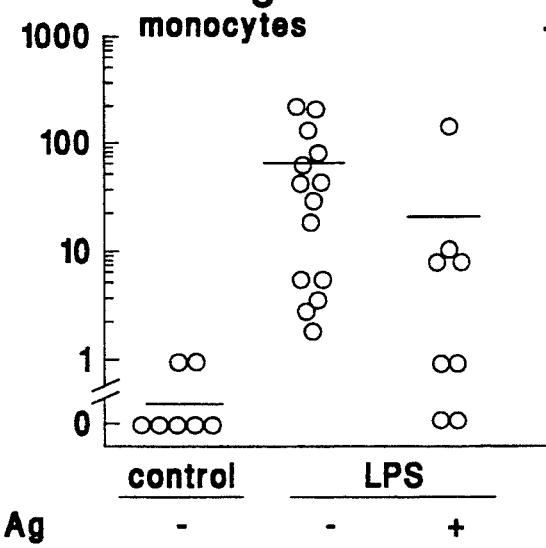
Figure 3D:
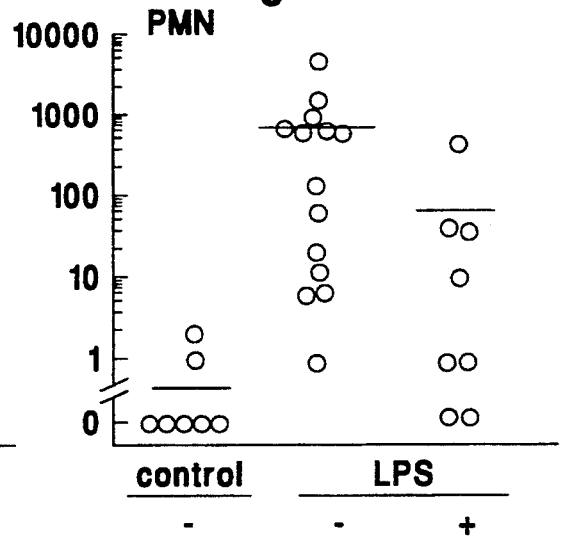

FIG. 3 in four parts, FIGS. 3A, 3B, 3C and 3D, is a graphical representation which shows aqueous fluid leukocyte cell counts in Lewis rats treated with 100 μg LPS. Cell counts of the aqueous fluid (FIG. 3A) and of three types of infiltrating cells into the aqueous fluid (FIG. 3B, lymphocytes; FIG. 3C, monocytes; and FIG. 3D, PMN) are shown on a logarithmic scale on the y axis for controls (−) and for LPS before (−) and after (+) treatment with 100 mg/Kg aminoguanidine (Ag) on the x axis. Each filled in circle (•) represents the cell count from an individual rat.

Figure 4:
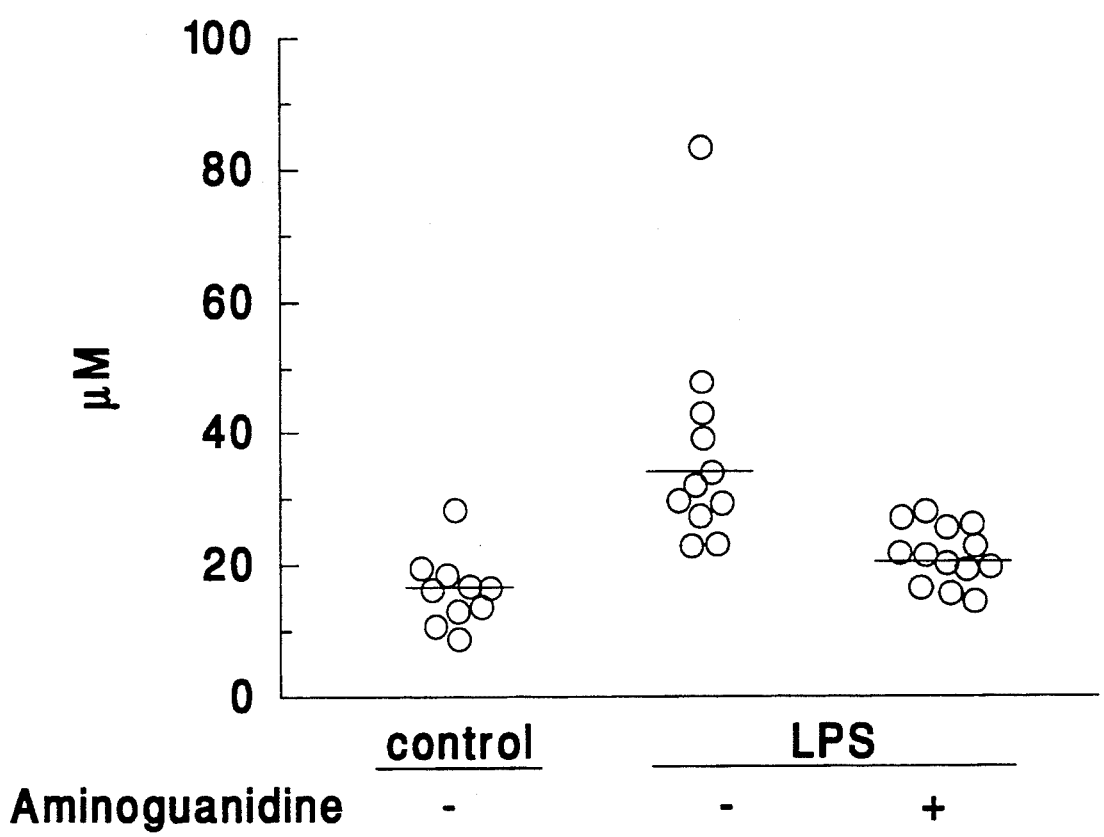
FIG. 4 is a graphical representation of the effect of aminoguanidine on plasma nitrate/nitrile levels in Lewis rats treated with 100 µg LPS.

FIG. 4 is a graphical representation which shows the effect of aminoguanidine on plasma nitrate/nitrite levels in Lewis rats treated with 100 μg LPS. Plasma nitrate/nitrite levels in μg are shown on the y axis for control (−) and for LPS before (−) and after (+) treatment with 100 mg/Kg aminoguanidine.

In order to further illustrate the invention, the following detailed Examples were certain out although it should be understood that the invention is not limited to these specific Examples or the details described therein which are for illustrative and not limitative purposes. The results obtained in these Examples are further shown in Tables 1 to 4 hereinbelow and the accompanying FIGS. 1 to 4.

EXAMPLE 1

Endotoxin-induced acute uveitis and generalized vascular leakage: inhibition by aminoguanidine

Methods

Animals and materials

Male Lewis rats (~200 g) were purchased from Harlan Sprague Dawley (Indianapolis, Ind.) and housed and cared for in accordance with the guidelines of the Washington University Committee for the Humane Care of Laboratory Animals and in accordance with NIH guidelines on laboratory animal welfare. Rats were housed individually, fed standard rat chow (Ralston, Purina, Richmond, Ind.) and water ad libitum, and were on a 12 hour light/dark cycle. Aminoguanidine (hemisulfate), and lipopolysaccharide (LPS; *Salmonella minnesota*) were purchased from Sigma (St. Louis, Mo.) $^{125}$I and $^{46}$Sc microspheres were obtained from NEN Research Products (Boston, Mass.). $^{131}$I was obtained from ICN Biomedicals, Inc. (Costa Mesa, Calif.).

Induction of LPS-induced vascular injury

LPS was dissolved in sterile pyrogen-free 0.9% saline at concentrations of 1 μg/μl, and unless stated otherwise, 50 μl was injected into each hind footpad (100 μg total dose per rat) using metofane anesthesia as described previously by other investigators [Herbort et al., *Graefe's Arch. Clin. Exp. Ophthalmol.* 226, pp. 553–558 (1988); and Hoekzema et al., *Invest. Ophthalmol. Vis. Sci.* 33, pp. 532–539 (1992)]. Control rats received an equal volume of 0.9% saline. 100 mg/kg body weight aminoguanidine was injected subcutaneously in LPS-treated and in control rats in 0, 3, 6, 12, 18 and within 60 minutes of the initiation of the test, which corresponds to 20–24 hours after LPS injection.

Assessment of vascular function

Regional vascular albumin permeation was quantified by use of an isotope dilution technique based on the injection of bovine serum albumin (BSA) labeled with 2 different iodine isotope, $^{125}$I and $^{131}$I [Pugliese et al., *Metabolism* 39 pp. 690–697 (1990); Pugliese et al., *Diabe-* tes 39, pp. 323–332 (1990); and Pugliese et al., *Diabetes* 39, pp. 312–322 (1990)]. $^{125}$I-BSA was used to quantify vascular albumin filtration after 10 min. of tracer circulation while $^{131}$I-BSA served as a plasma volume marker for correction of $^{125}$I-BSA tissue activity for tracer contained within vessels. Purified monomer BSA (1 mg) was iodinated with 1 mCi of $^{131}$I or $^{125}$I by the iodogen method as previously described [Pugliese et al., *Diabetes.* 39, pp. 323–332 (1990)]

Rats were anesthetized with Inactin (Byk Gulden, Konstanz, FRG) (~100 mg/kg body weight injected i.p.), and core body temperature maintained at 37°±0.5° C. using heat lamps, a 37° C. surgical tray, and a rectal temperature probe. The left femoral vein, left iliac artery, and right subclavian artery were cannulated with polyethylene tubing (0.58 mm i.d.) filled with heparinized saline (400 U heparin/ml). The femoral vein cannula was used for tracer injection and the subclavian artery cannula was connected to a pressure transducer for blood pressure monitoring. The left iliac artery was connected to a 1 ml syringe attached to a Harvard Model 940 constant withdrawal pump preset to withdraw at a constant rate of 0.055 ml/min. The trachea was intubated and connected to a small rodent respirator for continuous ventilatory support. Microspheres were injected into the left ventricle through a carotid artery cannula.

At time 0, $^{125}$I-albumin was injected and the withdrawal pump was started simultaneously. Eight min. after time 0, $^{131}$I-BSA was injected, followed by the microspheres. At the 10 min mark, the heart was excised to stop all blood flow, the withdrawal pump was stopped simultaneously, and various tissues were sampled for gamma spectrometry.

The left eye was dissected as previously described [Pugliese et al., *Diabetes* 39, pp. 323–332 (1990); and Pugliese et al., *Diabetes* 39, pp. 312–322 (1990)] and all tissue samples and arterial plasma samples were weighed, then counted in a gamma spectrometer. A quantitative index of $^{125}$I-BSA tissue clearance was calculated as previously described in [Pugliese et al., *Metabolism* 39, pp. 690–697 (1990); Pugliese et al., *Diabetes* 39, pp. 323–332 (1990); Pugliese et al., and *Diabetes* 39, pp. 312–322 (1990)] and expressed as $\mu$g plasma/g tissue wet weight/min. Briefly, $^{125}$I-BSA tissue activity was corrected for tracer contained within the tissue vasculature by multiplying $^{125}$I-BSA activity in the tissue by the ratio of $^{125}$I-BSA/$^{131}$I-BSA activities in the arterial plasma sample obtained at the end of the test. The vascular-corrected $^{125}$I-BSA tissue activity was divided by the time-averaged $^{125}$I-BSA plasma activity (obtained from a well mixed sample of plasma taken from the withdrawal syringe) and by the tracer circulation time (10 min) and then normalized per g tissue wet weight. To calculate blood flow, total activity of $^{46}$Sc in each ocular tissue was divided by the activity of $^{46}$Sc in the reference blood sample obtained from the withdrawal pump syringe, multiplied by the pump withdrawal rate, and expressed as ml/g tissue/min [Pugliese et al. *Diabetes* 39, pp. 323–332 (1990) and Pugliese et al., *Diabetes* 39, pp. 312–322 (1990)]. Other non-ocular tissues (aorta, kidney, skin, skeletal muscle, sciatic nerve) also were sampled to assess if LPS induced a generalized vascular dysfunction.

Assessment of cells in aqueous humor

Aqueous fluid was collected from the left eye only (the right carotid artery was ligated for the blood flow studies and this eye was not used for function studies) using a 100 $\mu$l heparinized capillary tube and placed in a microfuge tube. Well mixed aliquots (2 $\mu$l) were spread on a siliconized glass slide, air dried, stained with Wright's stain, and the total number of cells and a differential cell count were performed using a Leitz orthoplan light microscope. Plasma nitrate/nitrite measurements Anticoagulated (heparin) plasma samples were centrifuged at 7500 rpm for 1 hour at 4° C. using a 10,000 molecular weight cut off Centricon filter (Amicon, Beverly, Mass.). Plasma nitrate was enzymatically reduced to nitrite using Aspergillus niger nitrate reductase (Sigma, St. Louis, Mo.). Briefly, the sample was incubated with 40 $\mu$M NADPH and 14 mU of enzyme in a final volume of 50 $\mu$l of 20 mM Tris, pH 7.6; the reaction was terminated after 5 minutes at 20° C. by dilution with 50 $\mu$l of water followed by addition of 10 $\mu$l of freshly prepared DAN reagent (0.05 mg/ml in 0.6M HCl) for determination of nitrite. The DAN assay is a modification of the conventional method of Damiani and Burini for the fluorometric determination of nitrite [*Talanta* 33, 649–652 (1986)]. 2,3-Diaminonaphthalene (DAN) is reacted with nitrite under acidic conditions to form 1-(H)-naphthotriazole, a fluorescent product. After a 10 minute incubation at 20° C., the reaction was terminated with 5 $\mu$of 2.8N NaOH, which maximizes the intensity of the fluorescent signal. Formation of the 2,3-diaminonaphthotriazole was measured using a Pandex (IDEXX Laboratories, Inc., Westbrook, Me.) fluorescent plate reader with excitation at 365 nm and emission read at 450 nm with a gain setting at 100%. Plasma nitrite levels were calculated by first subtracting the value of the enzyme blank (nitrate reductase plus NADPH) from the experimental reading, then calculating the value using a standard curve for nitrite to which NADPH was added.

Statistical analysis

All results are expressed as means ± standard deviations. Overall differences among test groups for each parameter were first assessed by the Van der Waerden test, and individual pair-wise group comparisons were evaluated by at least square means analysis only if the Van der Waerden test was significant at $p<0.05$ for a given parameter. A nonparametric Blom transformation of all data was performed prior to assessment of individual pair-wise group differences.

Results

Generalized vascular leakage of $^{125}$I-albumin

In preliminary tests, 50, 100, and 200 $\mu$g LPS were injected either as a single injection into one hind footpad or as a divided dose injected into both hind footpads of Lewis rats. In general, increases in $^{125}$I-albumin leakage were greater for the divided dose of LPS versus a single injection. FIG. 1 shows changes in $^{125}$I-albumin leakage expressed as a fold increase over control values for LPS given as a divided dose. Except for sciatic nerve, maximal increases in $^{125}$I-albumin leakage normalized to control values were observed with 100 $\mu$g LPS and this dose was selected for subsequent tests.

Table 1 shows changes in $^{125}$I-albumin permeation resulting from the injection of 100 $\mu$g LPS (50 $\mu$g/footpad) into footpads of Lewis rats. The Van der Waerden test indicated highly significant group differences for $^{125}$I-albumin leakage in the retina, anterior uvea, choroid/sclera, and aqueous fluid ($p<0.0001$), while changes were absent in brain. At the dose and frequency used, aminoguanidine attenuated the LPS-induced $^{125}$I- albumin leakage by ~75% in the retina, sciatic nerve, and aorta, by ~50% in the aqueous fluid and anterior uvea, and by ~30% in the posterior uvea, without affecting $^{125}$I-albumin leakage in controls.

FIG. 2 shows changes in regional blood flows expressed as a fold increase over control values for LPS administered as a divided dose. Regional blood flows increased with increasing dose of LPS in the anterior and posterior uveal vasculatures and in the heart, plateaued in the retinal and sciatic nerve at 100 µg LPS, and was unaffected by LPS in the kidney when measured 20 hours after LPS injection. The Van der Waerden test indicated significant group differences for blood flow in the anterior uvea and choroid/sclera but not in the retina, sciatic nerve, brain, heart, and kidney (Table 2). LPS increased blood flow ~40% in the anterior uvea and ~25% in the choroid-sclera and these increases were prevented by aminoguanidine.

Gravimetric and hemodynamic parameters

All gravimetric and hemodynamic parameters, including body weight, mean arterial blood pressure, cardiac output, cardiac index, total peripheral resistance, GFR (normalized either to whole kidney or g kidney wet weight), glomerular filtration fraction, and renal vascular resistance, were unaffected by the injection of 100 µg LPS (Table 3).

Aqueous fluid leukocyte cell counts

Number of cells in a well mixed 2 µl sample of aqueous fluid from controls was low, ranging from no cells in 6 animals to ~25 cells in 2 rats (FIG. 3); the median value was ~5 cells/2 µl fluid and was unaffected by aminoguanidine treatment in controls. As shown in FIG. 3A, 100 µg LPS significantly increased the number of cells in 2 µl of aqueous fluid. FIG. 3 also shows the types of infiltrating cells into the aqueous fluid following LPS injection. Virtually all cells in the aqueous fluid of controls (±aminoguanidine) were lymphocytes. In aqueous fluid of rats treated with 100 µg LPS, lymphocytes (FIG. 3B), monocytes (FIG. 3C), and PMNs (FIG. 3D) increased significantly with the largest increase observed for PMNs. Aminoguanidine reduced the total number of cells in the aqueous fluid of LPS-treated rats, including ~90% reduction in the number of PMNs.

Plasma nitrate/nitrite measurement

Plasma nitrate/nitrite levels were 17.9±8.6 µM for controls and were increased ~65% in LPS-treated rats (FIG. 4). Aminoguanidine treatment prevented the LPS-induced increases in plasma nitrate/nitrite levels.

It is seen from the above results that aminoguanidine markedly attenuated manifestations of endotoxin-induced acute uveitis (vascular leakage, increased blood flow, and exudation of leukocytes into the aqueous fluid) as well as elevated plasma nitrate/nitrite levels. Aminoguanidine also significantly attenuated or completely prevented systemic effects of endotoxin on vascular leakage, i.e., edema (an important manifestation/consequence of inflammation) in nerve, aorta, and small intestine.

TABLE 1

Effects of LPS (100 µg) and aminoguanidine (100 mg/kg) on Regional $^{125}$I-albumin permeation (µg plasma/min/g wet weight)

| | control | LPS | LPS + aminoguanidine |
|---|---|---|---|
| number of rats | 14 | 19 | 11 |
| eye | | | |
| aqueous fluid | 65 ± 23[a] | 294 ± 81[b] | 204 ± 53[b,f] |

TABLE 1-continued

Effects of LPS (100 µg) and aminoguanidine (100 mg/kg) on Regional $^{125}$I-albumin permeation (µg plasma/min/g wet weight)

| | control | LPS | LPS + aminoguanidine |
|---|---|---|---|
| anterior uvea | 270 ± 53 | 611 ± 110[b] | 423 ± 67[b,e] |
| posterior uvea | 258 ± 75 | 612 ± 110[b] | 497 ± 96[b,f] |
| retina | 66 ± 14 | 154 ± 32[b] | 86 ± 23[e] |
| sciatic nerve | 62 ± 14 | 167 ± 35[b] | 91 ± 20[c,e] |
| aorta | 75 ± 26 | 245 ± 64[b] | 114 ± 43[d,e] |
| skeletal muscle | 44 ± 17 | 62 ± 11 | 51 ± 10 |
| skin | 110 ± 27 | 209 ± 73[b] | 186 ± 49[c] |
| brain | 23 ± 11 | 24 ± 11 | 25 ± 15 |
| heart | 621 ± 57 | 585 ± 116 | 624 ± 86 |
| small intestines | 377 ± 112 | 567 ± 247[d] | 375 ± 100[g] |
| kidney | 612 ± 212 | 1,173 ± 407[b] | 1,578 ± 251[b,f] |

Male, Lewis rats were treated with 100 µg LPS (50 µg in each hind footpad) ± 100 mg/kg body weight aminoguanidine hemisulfate (at the time of injection of LPS and 3, 6, 12, 18, and 20–24 hours thereafter). LPS was injected at noon and the animals were sacrificed the following morning.
[a]values are mean ± SD
Significantly different from controls by least square means analysis:
[b]$p < 0.0001$;
[c]$p < 0.001$;
[d]$p < 0.05$
Significantly different from LPS-treated rats least square means analysis:
[e]$p < 0.0001$;
[f]$p < 0.005$;
[g]$p < 0.05$

TABLE 2

Effects of LPS (100 µg) and aminoguanidine (100 mg/kg) on regional blood flows (ml/min/g wet weight)

| | control | LPS | LPS + aminoguanidine |
|---|---|---|---|
| number of rats | 11 | 13 | 9 |
| eye | | | |
| anterior uvea | 1.8 ± 0.4 | 2.5 ± 0.6[b] | 1.9 ± 0.3[d] |
| posterior uvea | 3.4 ± 0.6 | 4.3 ± 0.9[c] | 3.7 ± 0.4 |
| retina | 0.42 ± 0.03 | 0.45 ± 0.07 | 0.42 ± 0.04 |
| sciatic nerve | 0.07 ± 0.01 | 0.08 ± 0.03 | 0.08 ± 0.03 |
| brain | 0.6 ± 0.1 | 0.6 ± 0.1 | 0.6 ± 0.1 |
| heart | 4.9 ± 1.4 | 6.1 ± 1.2 | 5.4 ± 1.7 |
| kidney | 4.8 ± 0.9 | 4.7 ± 0.6 | 4.9 ± 0.6 |

Male, Lewis rats were treated with 100 µg LPS (50 µg in each hind footpad) ± 100 mg/kg body weight aminoguanidine hemisulfate (at he time of injection of LPS and 3, 6, 12, 18, and 20–24 hours thereafter). LPS was injected at noon and the animals were sacrificed the following morning.
[a]values are mean ± SD
Significantly different from controls by least square means analysis:
[b]$p < 0.0001$;
[c]$p < 0.005$
Significantly different from LPS-treated rats least square means analysis:
[d]$p < 0.005$

TABLE 3

Effects of LPS (100 µg) and aminoguanidine (100 mg/kg) on gravimetric and hemodynamic parameters

| | control | LPS | LPS + aminoguanidine |
|---|---|---|---|
| number of rats | 5 | 6 | 7 |
| body weight (g) | 237 ± 15[a] | 225 ± 9 | 229 ± 12 |
| mean arterial blood pressure (mm Hg) | 120 ± 9 | 121 ± 9 | 124 ± 10 |
| cardiac output (ml/min) | 81 ± 9 | 75 ± 4 | 77 ± 3 |
| cardiac index (ml/min/100 g b.w.) | 343 ± 19 | 334 ± 13 | 336 ± 23 |
| total peripheral resistance (mm Hg/ml/min) | 1.42 ± 0.10 | 1.55 ± 0.14 | 1.54 ± 0.11 |
| GFR (ml/min/whole kidney) | 0.96 ± 0.07 | 0.97 ± 0.06 | 0.95 ± 0.14 |
| GFR (ml/min/g kidney) | 0.87 ± 0.07 | 0.90 ± 0.11 | 0.87 ± 0.15 |
| filtration | 0.34 ± 0.08 | 0.34 ± 0.05 | 0.31 ± 0.06 |

TABLE 3-continued

Effects of LPS (100 μg) and aminoguanidine (100 mg/kg) on gravimetric and hemodynamic parameters

| | control | LPS | LPS + aminoguanidine |
|---|---|---|---|
| fraction (GFR/renal blood flow) | | | |
| renal vascular resistance (mm Hg/ml/min) | 0.97 ± 0.07 | 0.97 ± 0.06 | 0.95 ± 0.14 |

Male, Lewis rats were treated with 100 μg LPS (50 μg in each hind footpad) ± 100 mg/kg body weight aminoguanidine hemisulfate (at the time of injection of LPS and 3, 6, 12, 18, and 20-24 hours thereafter). LPS was injected at noon and the animals were sacrificed the following morning.
$^a$values are mean ± SD

EXAMPLE 2

Endotoxin-induced acute uveitis and generalized vascular leakage: inhibition by methylguanidine Methods Animals and materials Male Lewis rats (~200 g) were purchased from Harlan Sprague Dawley (Indianapolis, Ind.) and housed and cared for in accordance with the guidelines of the University Committee for the Humane Care of Laboratory Animals in accordance with NIH guidelines on laboratory animal welfare. Rats were housed individually, fed standard rat chow (Ralston Purina, Richmond, Ind.) and water ad libitum, and were on a 12 hour light-/dark cycle. Methylguanidine (hydrochloride) and lipopolysaccharide (LPS; *Salmonella minnesota*) were purchased from Sigma (St. Louis, Mo.). $^{125}$I was obtained from NEN Research Products (Boston, Mass.). $^{131}$I was obtained from ICN Biomedicals, Inc. (Costa Mesa, Calif.).

Induction of LPS-inducted vascular injury

LPS was dissolved in sterile pyrogen-free 0.9% saline at concentrations of 1 μ/μl, and 50 μwas injected into each hind footpad (100 μg total dose per rat) using metofane anesthesia as described previously by other investigators [Herbort et al., *Graefe's Arch. Clin. Exp. Ophthalmol.* 226, pp. 553-558 (1988); and Hoekzema et al., *Invest. Ophthalmol. Vis. Sci.* 33, pp. 532-539 (1992)]. Control rats received an equal volume of 0.9% saline. 50 mg/kg body weight methylguanidine was injected subcutaneously in LPS-treated and in control rats at 0, 3, 6, 12, 18 and 20-24 hours after LPS injection. Animals were killed for the vascular function studies 20 to 24 hours after LPS injection.

Assessment of vascular function

Regional vascular albumin permeation was quantified by use of an isotope dilution technique based on the injection of bovine serum albumin (BSA) labeled with 2 different iodine isotopes, $^{125}$I and $^{131}$I [Pugliese et al., *Metabolism* 39, pp. 690-697 (1990); Pugliese et al., *Diabetes* 39, pp. 323-332 (1990); and Pugliese et al., *Diabetes* 39 pp. 312-322 (1990)]. $^{125}$I-BSA was used to quantify vascular albumin filtration after 10 min of tracer circulation, while $^{131}$I-BSA served as a plasma volume marker for correction of $^{125}$I-BSA tissue activity for tracer contained within vessels. Purified monomer BSA (1 mg) was iodinated with 1 mCi of $^{131}$I or $^{125}$I by the iodogen method as previously described in Pugliese et al., *Diabetes* 39 pp. 323-332 (1990).

Rats were anesthetized with Inactin (Byk Gulden Konstanz, FRG) (~100 mg/kg body weight injected i.p.), and core body temperature maintained at 37° ±0.5° C. using heat lamps, a 37° C. surgical tray, and a rectal temperature probe. The left femoral vein, left iliac artery, and right subclavian artery were cannulated with polyethylene tubing (0.58 mm i.d.) filled with heparinized saline (400 U heparin/ml). The femoral vein cannula were used for tracer injection and the subclavian artery cannula was connected to a pressure transducer for blood pressure monitoring. The left iliac artery was connected to a 1 ml syringe attached to a Harvard Model 940 constant withdrawal pump preset to withdraw at a constant rate of 0.055 ml/min. The trachea was intubated and connected to a small rodent respirator for continuous ventilatory support.

At time 0, $^{125}$I-albumin was injected i.v. and the withdrawal pump was started simultaneously. Eight min after time 0, $^{131}$I-BSA was injected. At the 10 min mark, the heart was excised to stop all blood flow, the withdrawal pump was stopped simultaneously, and various tissues were sampled for gamma spectrometry.

The left eye was dissected as previously described [Pugliese et al., *Diabetes* 39, pp. 323-332 (1990) and Pugliese et al., *Diabetes* 39, pp. 312-322 (1990)] and all tissue samples and arterial plasma samples were weighed, then counted in a gamma spectrometer. A quantitative index of $^{125}$I-BSA tissue clearance was calculated as previously described [Pugliese et al., *Metabolism* 39, pp. 690-697 (1990); Pugliese et al., *Diabetes* 39, pp. 323-332 (1990); and Pugliese et al., *Diabetes* 39, pp. 312-322 (1990)] and expressed as μg plasma/g tissue wet weight/min. Briefly, $^{125}$I-BSA tissue activity was corrected for tracer contained within the tissue vasculature by multiplying $^{125}$I-BSA activity in the tissue by the ratio of $^{125}$I-BSA/$^{131}$I-BSA activities in the arterial plasma sample obtained at the end of the test. The vascular-corrected $^{125}$I-BSA tissue activity was divided by the time-averaged $^{125}$I-BSA plasma activity (obtained from a well mixed sample of plasma taken from the withdrawal syringe) and by the tracer circulation time (10 min) and then normalized per g tissue wet weight. Other non-ocular tissues (aorta, kidney, skin, skeletal muscle, sciatic nerve) also were sampled to assess if LPS induced a generalized vascular dysfunction.

Statistical analysis

All results are expressed as means ± standard deviations. Overall differences among test groups for each parameter were assessed by Students' test.

Generalized vascular leakage of $^{125}$I-albumin

Table 4 shows changes in $^{125}$I-albumin permeation resulting from the injection of 100 μg LPS (50 μg/footpad) into footpads of Lewis rats. Highly significant group differences for $^{125}$I-albumin leakage were evident in the aqueous fluid, anterior uvea, choroid/sclera, retina, sciatic nerve, aorta, and kidney (p<0.0001), while smaller increases were observed in the skin and skeletal muscle. No LPS-induced changes were present in brain, heart, or small intestine. At the dose and frequency used, methylguanidine attenuated the LPS-induced $^{125}$I-albumin leakage in aqueous fluid, anterior uvea, and kidney and prevented the LPS-induced increases in albumin leakage in the choroid/sclera, retina, sciatic nerve, aorta, and skin.

It is seen from the above results that methylguanidine (at approximately one half of the dose of aminoguanidine used in Example 1) was as effective as (or more effective than) aminoguanidine in preventing endotoxin-induced vascular leakage (an important manifestation/consequence of inflammation) in uveal tissue as well as in the sciatic nerve, aorta, skeletal muscle, skin, and kidney.

Similar results as obtained in Examples 1 and 2 can be obtained by substituting N,N'-diaminoguanidine or 1,1-dimethylguanidine for equivalent amounts of aminoguanidine or methylguanidine, respectively, in said Examples.

TABLE 4

Effects of LPS and methylguanidine (mg) on regional $^{125}$I-albumin permeation$^a$

|  | control | LPS | LPS + Mg |
|---|---|---|---|
| number of rats | 5 | 8 | 4 |
| aqueous | 154 ± 100 | 494 ± 283$^a$ | 335 ± 30$^c$ |
| anterior uvea | 266 ± 52 | 618 ± 106$^a$ | 383 ± 32$^{c,e}$ |
| choroid/sclera | 298 ± 67 | 582 ± 77$^a$ | 357 ± 50$^d$ |
| retina | 68 ± 15 | 168 ± 28$^a$ | 67 ± 7$^d$ |
| sciatic nerve | 71 ± 14 | 187 ± 32$^a$ | 69 ± 3$^d$ |
| aorta | 75 ± 24 | 211 ± 43$^a$ | 102 ± 8$^d$ |
| skeletal muscle | 54 ± 19 | 103 ± 46$^c$ | 63 ± 11 |
| skin | 99 ± 29 | 224 ± 65$^b$ | 106 ± 16$^f$ |
| brain | 20 ± 4 | 25 ± 6 | 19 ± 5 |
| heart | 623 ± 43 | 699 ± 58 | 629 ± 82 |
| small intestine | 414 ± 40 | 559 ± 147 | 423 ± 188 |
| kidney | 635 ± 239 | 1561 ± 221$^a$ | 1042 ± 253$^{c,e}$ |

$^a$μg plasma/g wet weight/min; values are mean ± SD.
Male, Lewis rats were treated with 100 μg LPS (50 μg in each hind footpad) ± 50 mg/kg body weight methylguanidine hydrochloride (at the time of injection of LPS and 3, 6, 12, 18, and 20–24 hours thereafter). LPS was injected at noon and the animals were sacrificed the following morning.
Significantly different from untreated controls:
$^a$p < 0.0001;
$^b$p < 0.005;
$^c$p < 0.05
Significantly different from LPS:
$^d$p < 0.001;
$^e$p < 0.005;
$^f$p < 0.01

The inhibitors of nitric oxide formation described herein can be used for administration to warm blooded mammals by conventional means, preferably in formulations with pharmaceutically acceptable diluents and carriers. The amount of the active inhibitor to be administered must be an effective amount, that is, an amount which is medically beneficial but does not present toxic effects which overweigh the advantages which accompany its use. It would be expected that the adult human daily dosage would normally range upward from about one milligram per kilo of body weight of the drug. A suitable route of administration is orally in the form of capsules, tablets, syrups, elixirs and the like, although parenteral administration also can be used, e.g. intravenously, intraperitoneally or subcutaneously. Intraveneous administration of the drug in aqueous solution such as physiologic saline is illustrative. Appropriate formulations of the drug in pharmaceutically acceptable diluents and carriers in therapeutic dosage form can be prepared by reference to general texts in the field such as, for example, Remington's Pharmaceutical Sciences, Ed. Arthur Osol. 16th ed., 1980, Mack Publishing Co., Easton, Pa.

Various other examples will be apparent to the person skilled in the art after reading the present disclosure without departing from the spirit and scope of the invention. It is intended that all such examples be included within the scope of the appended claims.

What is claimed is:

1. A method of inhibiting nitric oxide production in a warm blooded mammal afflicted with physiological conditions manifested by an acute or inflammatory disease which is not immunologically-mediated which comprises administering to said mammal a nitric oxide inhibitory effective amount of an inhibitory compound selected from the group consisting of aminoguanidine, N,N'-diaminoguanidine, methylguanidine and 1,1'-dimethylguanidine.

2. The method of claim 1 in which the inhibitory compound is aminoguanidine.

3. The method of claim 1 in which the inhibitory compound is N,N'-diaminoguanidine.

4. The method of claim 1 in which the inhibitory compound is methylguanidine.

5. The method of claim 1 in which the inhibitory compound is 1,1-dimethylguanidine.

6. The method of claim 1 in which the inflammatory disease is uveitis.

7. The method of claim 6 in which the inhibitory compound is aminoguanidine.

8. The method of claim 6 in which the inhibitory compound is N,N'-diaminoguanidine.

9. The method of claim 6 in which the inhibitory compound is methylguanidine.

10. The method of claim 6 in which the inhibitory compound is 1,1-dimethylguanidine.

* * * * *

UNITED STATES PATENT AND TRADEMARK OFFICE
CERTIFICATE OF CORRECTION

PATENT NO. : 5,358,969
DATED : October 25, 1994
INVENTOR(S) : J.R. Williamson, J.A. Corbett, M.L. McDaniel and R.G. Tilton It is certified that error appears in the above-indentified patent and that said Letters Patent is hereby corrected as shown below:

At col. 2, line 40, "nitrile" should read --nitrite--.

At col. 4, line 21, "certain" should read --carried--.

At col. 9, line 39, "1 μ/μl" should read --1 pg/μl--.

At col. 9, line 39, "50 μ" should read --50 μl--.

At col. 12, line 20 (Claim 1, line 3), cancel "or".

Signed and Sealed this

Eleventh Day of June, 1996

Attest:

BRUCE LEHMAN

Attesting Officer

Commissioner of Patents and Trademarks